(12) United States Patent
Downey et al.

(10) Patent No.: US 11,364,065 B2
(45) Date of Patent: Jun. 21, 2022

(54) SYSTEMS AND METHODS TO ENHANCE RADIAL SPRAY FROM A CATHETER

(71) Applicant: CSA Medical, Inc., Lexington, MA (US)

(72) Inventors: George A. Downey, Arlington, MA (US); John P. O'Connor, Andover, MA (US)

(73) Assignee: CSA Medical, Inc., Lexington, MA (US)

( * ) Notice: Subject to any disclaimer, the term of this patent is extended or adjusted under 35 U.S.C. 154(b) by 680 days.

(21) Appl. No.: 16/131,532

(22) Filed: Sep. 14, 2018

(65) Prior Publication Data
US 2019/0083158 A1 Mar. 21, 2019

Related U.S. Application Data

(60) Provisional application No. 62/559,061, filed on Sep. 15, 2017.

(51) Int. Cl.
*A61B 18/02* (2006.01)
*A61B 18/00* (2006.01)

(52) U.S. Cl.
CPC ...... *A61B 18/0218* (2013.01); *A61B 2018/00488* (2013.01); *A61B 2018/00494* (2013.01); *A61B 2018/00577* (2013.01); *A61B 2018/0212* (2013.01)

(58) Field of Classification Search
CPC ...... A61B 18/0218; A61B 2018/00488; A61B 2018/00494; A61B 2018/00577; A61B 2018/0212
See application file for complete search history.

(56) References Cited

U.S. PATENT DOCUMENTS

| | | | | |
|---|---|---|---|---|
| 4,533,345 A | * | 8/1985 | Louw | A61B 17/42 604/43 |
| 6,027,499 A | * | 2/2000 | Johnston | A61B 18/0218 600/104 |
| 6,077,257 A | * | 6/2000 | Edwards | A61B 18/12 604/506 |
| 6,974,456 B2 | * | 12/2005 | Edwards | A61B 18/1477 606/41 |
| 2002/0143323 A1 | * | 10/2002 | Johnston | A61B 34/35 606/21 |
| 2003/0032936 A1 | * | 2/2003 | Lederman | A61B 18/1492 604/507 |
| 2009/0192505 A1 | * | 7/2009 | Askew | A61M 16/0463 606/21 |

(Continued)

FOREIGN PATENT DOCUMENTS

JP 2003505140 A 2/2003
WO 0106942 A1 2/2001

OTHER PUBLICATIONS

International Search Report and Written Opinion for PCT/US2018/051067, dated Feb. 1, 2019, 11 pages.

*Primary Examiner* — Michael F Peffley
*Assistant Examiner* — Amanda L Zink
(74) *Attorney, Agent, or Firm* — Goodwin Procter LLP (57) ABSTRACT

The present disclosure relates generally to the field of medical devices. In particular, the present disclosure relates to methods and devices to enhance radial spray from a catheter. Extension devices for a radial spray catheter, including radial cryospray catheters, are disclosed.

17 Claims, 6 Drawing Sheets

(56) References Cited

U.S. PATENT DOCUMENTS

| | | | | |
|---|---|---|---|---|
| 2010/0057065 A1* | 3/2010 | Krimsky | ............ | A61B 18/0218 606/21 |
| 2011/0092892 A1* | 4/2011 | Nitsan | ................ | A61M 3/0283 604/28 |
| 2013/0253491 A1* | 9/2013 | Burr | .................. | A61B 18/0218 606/21 |
| 2015/0045786 A1* | 2/2015 | Edwards | ............ | A61B 18/1492 606/34 |
| 2015/0066005 A1* | 3/2015 | Fan | .................... | A61B 18/0218 606/21 |
| 2015/0351822 A1* | 12/2015 | Mulcahey | .......... | A61B 18/0218 606/22 |
| 2019/0255281 A1* | 8/2019 | Mulcahey | .......... | A61B 18/0218 |

* cited by examiner

SYSTEMS AND METHODS TO ENHANCE RADIAL SPRAY FROM A CATHETER

PRIORITY

The application claims the benefit of priority under 35 USC § 119 to U.S. Provisional Patent Application Ser. No. 62/559,061, filed Sep. 15, 2017, which is incorporated by reference herein in its entirety and for all purposes.

FIELD

The present disclosure relates generally to the field of medical devices. In particular, the present disclosure relates to methods and devices to enhance radial spray from a catheter. Extension devices for a radial spray catheter, including radial cryospray catheters, are disclosed.

BACKGROUND

Various catheters are used within different body lumens for different applications, including to deliver fluids, as a diagnostic or treatment option, to the body lumen. The fluid may be a liquid, a gas, or a mixture of both a liquid and a gas. The delivery may involve spraying the fluid on the wall of the body lumen. In some cases, the efficacy and/or efficiency of the procedure may be dependent on how close to or far away from the body lumen the fluid is delivered from the catheter. For purposes of delivering a catheter through an endoscope within a body lumen, the profile of the catheter has a certain diameter. When extended outside of the scope that profile may result in the catheter being less than an optimum distance from the lumen wall for efficient delivery of the fluid.

As an example, cryosurgery is a procedure in which diseased, damaged or otherwise undesirable tissue (collectively referred to herein as "target tissue") is treated by focal delivery of a cryogen under pressure, which may be a cryogen spray. These systems are typically referred to as cryoablation systems, cryospray systems, cryospray ablation systems, cryosurgery systems, cryosurgery spray systems and/or cryogen spray ablation systems. As typically used, "cryogen" refers to any fluid (e.g., gas, liquefied gas or other fluid known to one of ordinary skill in the art) with a sufficiently low boiling point (i.e., below approximately −153° C.) for therapeutically effective use during a cryogenic surgical procedure. Suitable cryogens may include, for example, liquid argon, liquid nitrogen and liquid helium. Pseudo-cryogens such as carbon dioxide and liquid nitrous oxide that have a boiling temperature above −153° C. but still very low (e.g., −89° C. for $N_2O$) may also be used.

During operation of a cryospray system, a medical professional (e.g., clinician, technician, medical professional, surgeon etc.) directs a cryogen spray onto the surface of a treatment area via a cryogen delivery catheter. The medical professional may target the cryogen spray visually through a video-assisted device or endoscope, such as a bronchoscope, gastroscope, colonoscope, or ureteroscope. Cryogen spray exits the cryogen delivery catheter at a temperature ranging from 0° C. to −196° C., causing the target tissue to freeze or "cryofrost."

Body lumens (e.g., the esophagus, trachea, intestines, etc.) may be treated with cryoablation via radial spray from a catheter. However, as noted above, catheters generally have a low profile for insertion into the body and therefore the radial apertures in the catheter may be remote from the target tissue for treatment. This distance may cause inefficiencies in cryoablation treatment due to spray field interactions from apertures, for example mixing, entrainment, cross-currents and viscous losses, resulting in low tissue coverage and increased therapy time. Various advantages may therefore be realized by the devices, systems and methods of the present disclosure for enhancing radial spray from catheters.

SUMMARY

The present disclosure in its various embodiments includes methods and devices to enhance radial spray from a catheter. Various embodiments may include extension devices for a radial spray catheter and/or a radial cryospray catheter. Various embodiments may be used with cryosurgery systems configured to laterally extend cryospray gases from a catheter to the target tissue within a body lumen. Extension devices for a radial spray catheter, including radial cryospray catheters and plugs, may emit spray more efficiently and may result in more effective treatment for targeted tissue. Extension devices for radial cryospray catheters or other devices, or radial cryospray catheters or other devices with extended radial apertures may allow for better reorientation of what may be substantially axial components of the flow of cryogens into more lateral spray plumes (such as generally normal to the target tissue) for a more efficient and effective treatment of cryospray. Extension devices may also bring cryospray closer to the target tissue.

In one aspect, an extension device for a radial spray catheter may comprise an elongate member with a first open end, a second end, and an elongate lumen therebetween. At least one extension member may extend from the elongate member with a first open end in fluid communication with the elongate lumen at one end, a second open end, and an extension lumen therebetween. The extension member(s) may be configured to substantially align with at least one radial aperture in a distal end of a catheter. The second end of the elongate member may be closed. An extension device may include a body at the second end of the elongate member that may have a diameter larger than a diameter of an outer surface of the elongate member. A body may have an outer diameter that is dimensioned to be larger than a spray lumen of a catheter. A body may have an atraumatic distal portion. A body may be dome-shaped. The extension member(s) may extend radially with respect to a central axis of the elongate lumen. The extension member(s) may be integral with the elongate member. The extension device may include silicone. The extension member(s) may have a length that is configured to extend an effective diameter of a catheter by at least 50%. The radial spray catheter may be a cryospray catheter that delivers cryospray through at least one radial aperture. A diameter of the extension member(s) may be smaller or larger than a diameter of the at least one radial aperture and the diameters may transition conically. The extension member(s) may be configured to lay substantially parallel to the elongate lumen in a relaxed state and extend radially outward in an activated state. The activated state may include a cryospray being delivered under pressure through the extension lumen. The elongate member may be configured for insertion into the distal end of a catheter.

In another aspect, an extension device for a radial spray catheter may comprise an elongate member with a proximal open end, a closed distal end, and an elongate lumen therebetween. The extension member(s) may extend from the elongate member with a first open end in fluid communication with the elongate lumen, a second open end, and an extension lumen therebetween. The extension member(s) may have an inverted state and an extended state. The extension member(s) may be configured to substantially align with at least one radial aperture in a distal end of the catheter. The extension lumen may have a diminishing diameter that diminishes from the first end to the second end. The extension member(s) may be inverted within the elongate member in the inverted state and may extend radially outward from the elongate member in the extended state. The second open end of the extension member(s) may be inverted within the extension lumen in the inverted state and may be extended outward from the extension lumen in the extended state. A body may be at the closed distal end of the elongate member. The extension lumen may be responsive to pressure from fluid supplied through the catheter to extend the extension member(s) through the at least one radial aperture. The extension lumen may be responsive to pressure from fluid supplied through the catheter to extend the extension member(s) into a substantially straight configuration.

In another aspect, a radial extension catheter for radial spray may comprise a catheter with a first open end, a second end, and a catheter lumen therebetween. At least one radial aperture may be at the second end. The extension member(s) may extend from the at least one radial aperture with a first open end in fluid communication with the catheter lumen, a second open end, and an extension lumen therebetween. The extension member(s) may be integral with the catheter lumen. The extension member(s) may extend from a body that may be inserted into the second end of the catheter. The extension member(s) may be configured to lay substantially parallel to the catheter lumen in a relaxed state and extend radially outward in an activated state. The second open end of the extension member(s) may be inverted within the catheter lumen in an inverted state and may be extended outward from the catheter lumen in an extended state. The extension lumen may have a diminishing diameter that diminishes from the first end to the second end. The extension member(s) may have a length that is configured to extend an effective diameter of the catheter by at least 50%.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs. Although embodiments of the present disclosure are described with specific reference to radial cryospray systems for use within the upper and lower GI tracts and respiratory system, it should be appreciated that such systems and methods may be used in a variety of other body passageways, organs and/or cavities, such as the vascular system, urogenital system, lymphatic system, neurological system and the like.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, portions, or the like, which are so conjoined, unless the context clearly indicates otherwise, and the conjunction "or" includes one or the others of the structures, components, portions, or the like, which are so conjoined, singly and in any combination and number, unless the context clearly indicates otherwise.

As used herein, the term "distal" refers to the end farthest away from the medical professional when introducing a device into a patient, while the term "proximal" refers to the end closest to the medical professional when introducing a device into a patient. As used herein, "diameter" refers to the distance of a straight line extending between two points and does not necessarily indicate a particular shape.

The present disclosure generally provides methods and devices to enhance radial spray from a catheter. Various embodiments may include extension devices for a radial spray catheter and/or a radial cryospray catheter.

For example, various embodiments, described here or otherwise, within the scope of the present disclosure, may be used with cryosurgery systems configured to laterally extend cryospray gases (hereafter referred to as "cryospray") from the catheter to the target tissue within a body lumen. Exemplary cryosurgery systems in which the present disclosure may be implemented include, but are not limited to, those systems described in U.S. Pat. Nos. 9,820,797, 9,301, 796 and 9,144,449, and U.S. patent application Ser. Nos. 14/012,320 and 14/869,814, each of which are herein incorporated by reference in their entirety.

Figure 1:
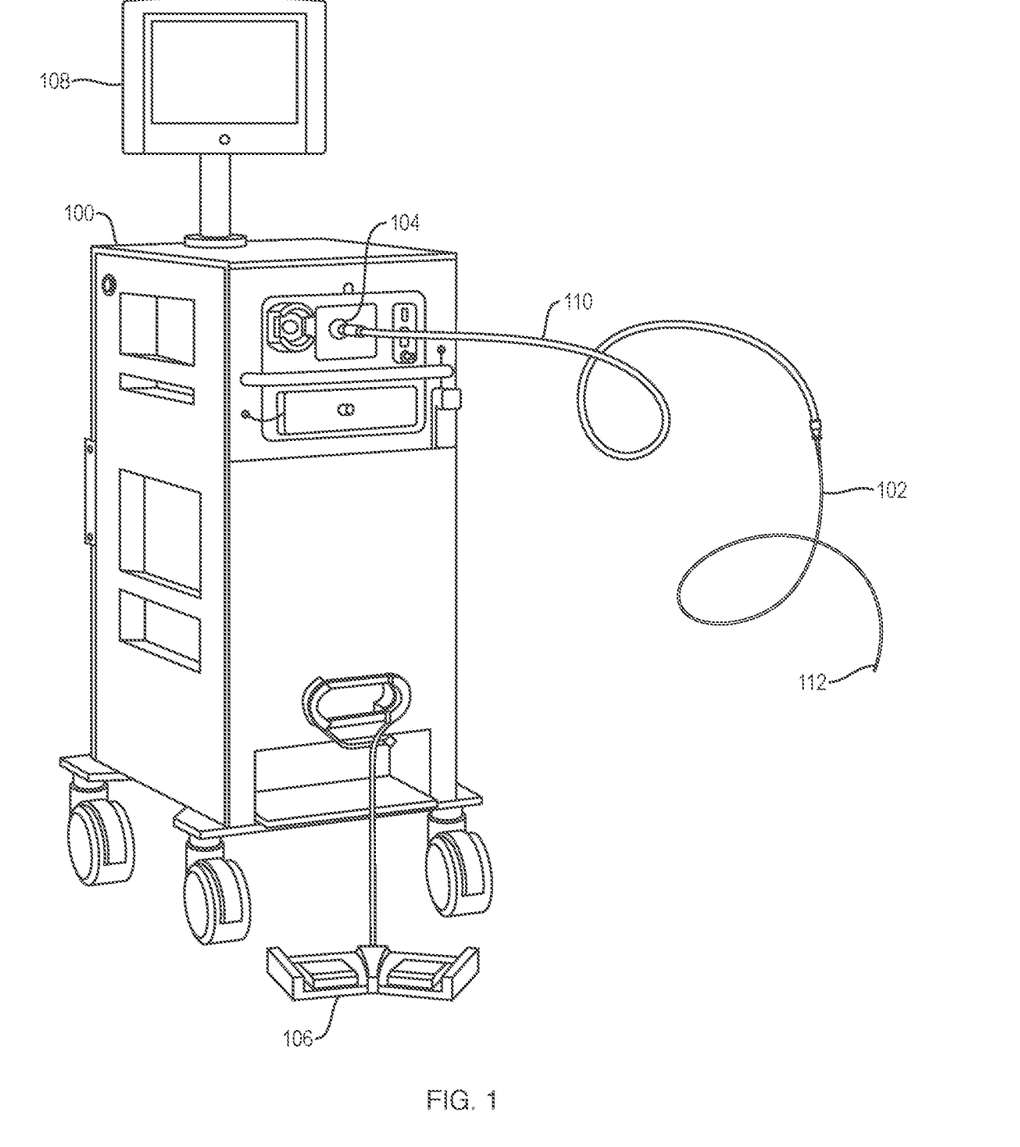
FIG. 1 illustrates an isometric view of a cryosurgery system in accordance with an embodiment of the present disclosure.

In one embodiment of a cyrospray delivery system configured to laterally extend cryospray from a catheter, as illustrated in FIG. 1, a catheter 102 is connected to a cryotherapy console 100 at a catheter interface 104. The catheter 102 may be used with an endoscope for delivery into a patient. An image received at the lens on the distal end of the endoscope may be transferred to a monitoring camera which sends video signals via a cable to the monitor 108, where the procedure can be visualized. Built-in software and controls in the console allows the medical professional to control delivery of cryogen from the tank through the catheter 102 via a foot petal 106. The catheter 102 may have an insulated portion 110 and a distal end 112.

As an example of the fluid mechanics of cryospray formation and supply, with reference to the system illustrated in FIG. 1, as cryogen (e.g., liquid nitrogen) travels from the tank to the proximal end of cryogen delivery catheter 102, the liquid warms and starts to boil, resulting in cool gas emerging from the distal end 112 of catheter 102. The amount of boiling in the catheter 102 depends on the mass, surface area, and thermal capacity of catheter 102. When the liquid nitrogen undergoes phase change from liquid to gaseous nitrogen, additional pressure is created throughout the length of catheter 102. This is especially true at a solenoid/catheter junction, where the diameter of the supply tube to the lumen of catheter 102 decreases, e.g., from approximately 0.25 inches to approximately 0.070 inches, respectively. The lumen of the catheter 102 may have a diameter, e.g., ranging between 0.030 and 0.115 inches. In an alternate embodiment, gas boiling inside the catheter 102 may be reduced even greater by the use of insulating materials such as PTFE, FEP, Pebax, and the like, or by surrounding the catheter with a substantially evacuated lumen to help reduce the rate of heat transfer.

With further reference to FIG. 1, as an example, the catheter 102 is connected to a console 100. The console 100 contains the tank that supplies the cryogen. The console 100 may include precooling and defrost features. The console 100 and/or catheter 102 include valving and plumbing to deliver the cryogen under pressure, e.g., delivering low pressure to the distal tip 112 of the catheter 102. There may be sensors within the console 100 and/or the catheter 102 to measure the temperature of the cryogen and/or the tissue. There may be a feedback loop for metered control of cryogen dosing. A pedal 106 may be used to control the cryogen delivery, or the cryogen delivery may be timed for a predetermined dosage. The distal tip 112 may be open-ended and/or include radial apertures. The console 100 may include software and/or hardware with safety features. The console 100 may include an interactive user interface. The console 100 may include control settings for a cryospray therapy procedure. The console 100 may include cryospray procedure profiles for pre-determined delivering of cryospray.

Figure 2:
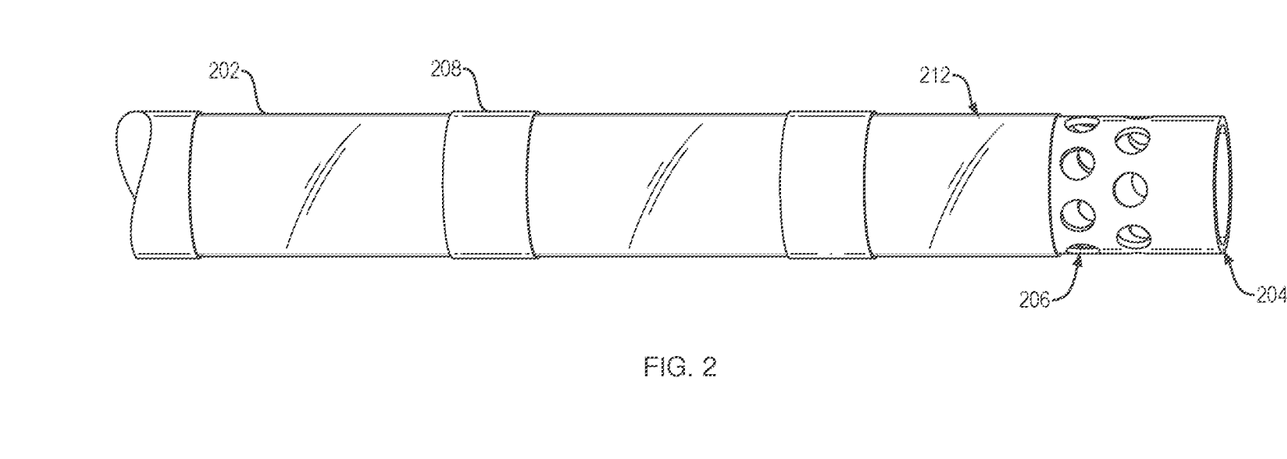
FIG. 2 illustrates a radial spray tip of a catheter in accordance with an embodiment of the present disclosure.

With reference to FIG. 2, an exemplary cyrospray catheter in accordance with embodiments of the present disclosure is illustrated. The catheter 202 is placed within a patient such that the distal end 212 is in proximity to the target tissue. A medical professional may visualize placement of the distal end 212 of the catheter 202 via a camera in an endoscope and/or through fluoroscopy. The marking bands 208 may be visualized using the camera and/or may be radiopaque for visualization with a fluoroscope. With the distal end 212 in position, the medical professional may introduce cryogen into the catheter 202. When the cryogen reaches the distal end 212 of catheter 202 it exits the distal tip 204 and/or the radial apertures 206 as a cyrospray towards the target tissue.

With the system of FIG. 1 and/or catheter of FIG. 2, for example, freezing of fluids on the target tissue and/or freezing of the target tissue is apparent to the medical professional by the acquisition of a white color by the target tissue. The white color, resulting from surface frost, indicates the onset of mucosal or other tissue freezing sufficient to initiate destruction of the diseased or abnormal tissue. The operator may use a system timer to freeze for a specified duration once initial cryofrost is achieved in order to control the depth of injury. The delivery of cyrogen may be metered and controlled via a feedback loop that monitors readings from one or more temperature sensors on the catheter shaft. The medical professional may observe the degree of freezing and stop the spray as soon as the surface achieves the desired whiteness of color. The operator may monitor the target tissue to determine when freezing has occurred via the camera integrated into the endoscope. The operator may manipulate the catheter to freeze the target tissue. Once the operation is complete, the catheter, endoscope, and any other instruments, such as a cryodecompression tube for the evacuation of fluids or gases from the patient, are withdrawn from the patient.

The delivery of a multiphase flow of cryogen through the catheter 202 leads to the radial apertures 206 and/or distal tip 204 for cryospray to exit the catheter. Cryogens may partially boil as they travel down the catheter 202 and the resulting mixture is released out of the exit points at the distal end 212 of the catheter 202. These exit points, as discussed above, may be remote from the target tissue since catheters generally have a low profile, e.g., for insertion through the working channel of an endoscope and into the body. The radial apertures 206 in the distal end 212 of the catheter 202 are meant to emit cryospray onto the inner wall of tissue in a body lumen.

When cryospray exits the distal end 212 of the catheter 202 through the radial holes 206, it does so typically in an orthogonal direction or angle from the catheter 202 (i.e., along an axis transverse to the longitudinal axis of the catheter). Increasing the ratio of length to diameter of these apertures may improve spray orthogonality, which may improve cooling efficiency. As the flow transitions from a longitudinal direction to a radial direction, a longer aperture (or lumen, nozzle, or the like) may allow for increased radial flow momentum. Cooling efficiency of the radial spray may be improved because the spray may impinge substantially normal to the tissue, reducing the amount of cryogen spray that is deflected when it hits warm tissue.

Figure 3:
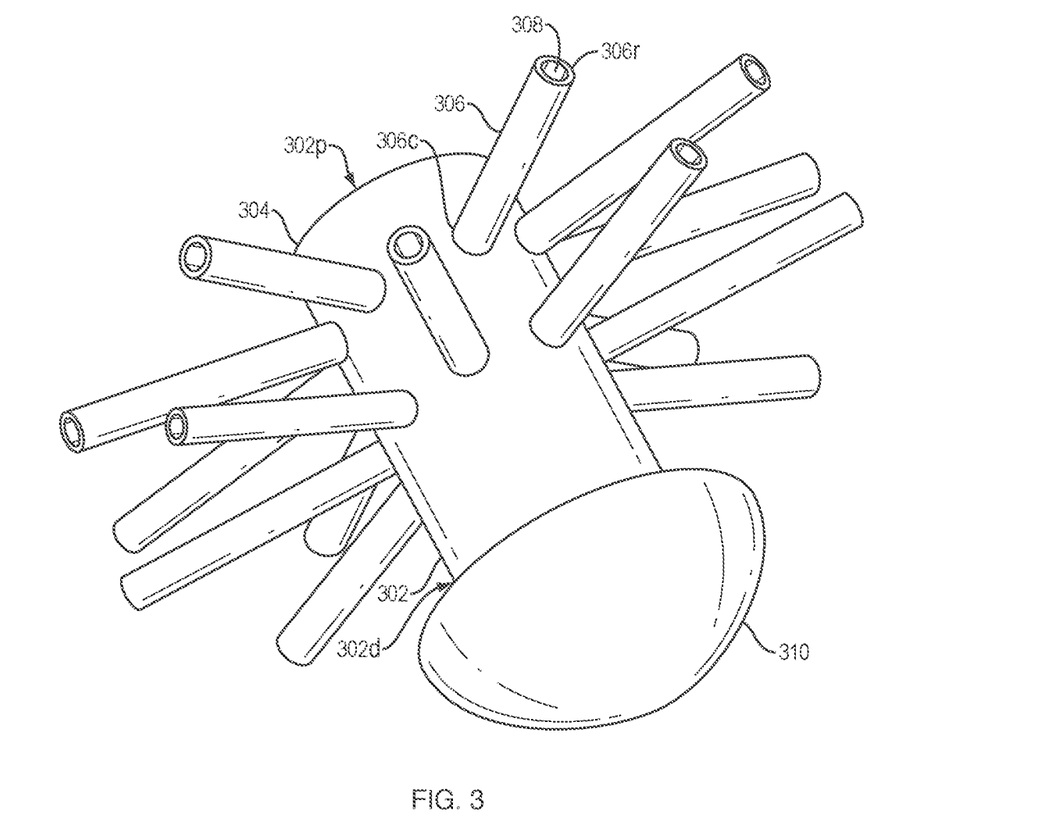
FIG. 3 illustrates an isometric view of an extension device in accordance with an embodiment of the present disclosure.

Referring to FIG. 3, an embodiment of an extension device for enhancing radial spray from a catheter according to the present disclosure includes an elongate member 302 with a proximal open end 302p, a distal end 302d, and an elongate lumen 304 between the ends. Numerous extension members 306 extend from the elongate member 302. The extension members 306 have a first open end 306c in fluid communication with the elongate lumen 304, a second open end 306r, and an extension lumen 308 between the ends. The extension members 306 extend radially from a central axis of the elongate lumen 304. The distal end 302d of the elongate member 302 is closed by a body 310. The body 310 has a diameter larger than a diameter of the outer surface of the elongate member 302. The body 310 has an atraumatic dome shape.

Figure 4:
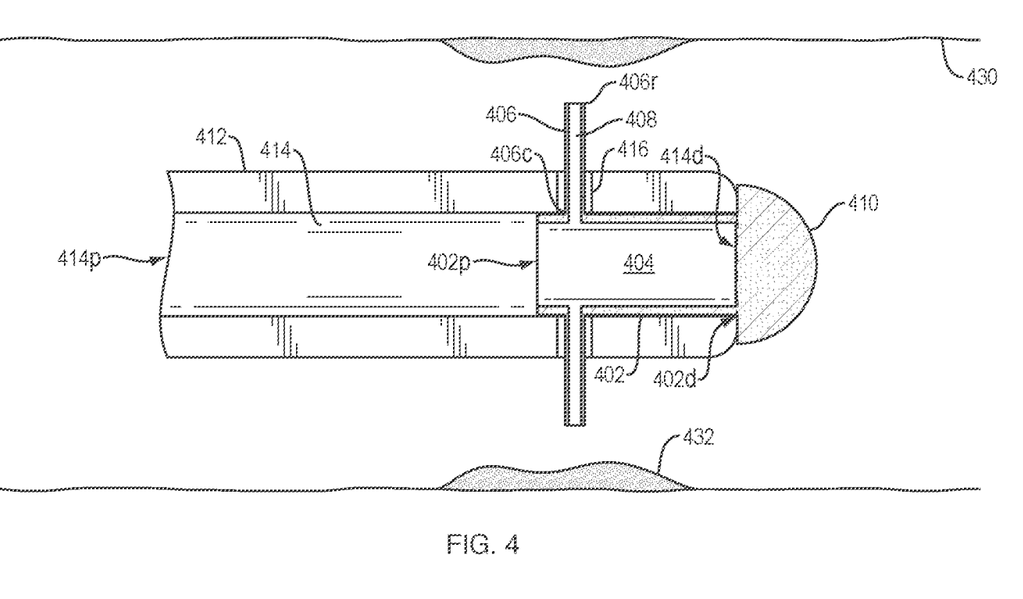
FIG. 4 illustrates a cross-sectional side view of a catheter and an extension device in accordance with an embodiment of the present disclosure.

Referring to FIG. 4, an embodiment of an extension device for a catheter 412 according to the present disclosure includes positioning an extension device, e.g., the device of FIG. 3, into the distal end of a catheter 412. The proximal open end 402p of the elongate member 402 is directed towards the proximal direction 414p of the catheter lumen 414. The distal end 402d of the elongate member 402 is directed towards the distal tip 414d of the catheter lumen 414 such that the body 410 abuts the distal tip 414d of the catheter lumen 414. The body 410 has a larger diameter than the lumen 414 such that it cannot be inserted into the lumen

414. Extension members 406 extend from the elongate member 402 through the radial apertures 416 that they align with.

One should appreciate that the cross-sectional view of FIG. 4 illustrates only a limited number of extension members, and that the inclusion of more extension members aligned in a first row around the circumference of the catheter with the extension members shown, and/or a second distal row of radial apertures 416 (206 in FIG. 2), such as illustrated in the catheter embodiment of FIG. 2, and corresponding extension members, is possible. As shown the two rows of apertures 206 are circumferentially offset from each other about a longitudinal axis of the catheter 202 such that a center point of the apertures 206 do not share the same cross-sectional plane between the proximal and distal rows of the apertures 206.

The extension devices of the present disclosure, e.g., the embodiment in FIG. 4, effectively brings the exit points for cryospray (i.e., the second ends 406r) closer to the target tissue 432 of a body lumen 432. The extension members 406 have a first open end 406c in fluid communication with the elongate lumen 404 at one end, a second open end 406r in close proximity to the target tissue 432, and an extension lumen 408 between the ends. With reference, for example to the system of FIG. 1, as cryogens are introduced to the proximal end of the catheter 102, the cryogens travel to the distal end of the catheter 412. As the cryogens travel from the tank and console 100 through the catheter, they are exposed to warmer temperatures and viscous resistance forces from the catheter 102, causing liquid cryogen to boil into cryospray gases. Once the mixed cryogens reach the distal end of the catheter 412, they enter the elongate lumen 404. The body 410 at the distal end 402d of the elongate lumen closes the lumen and prevents the cryogens from escaping out of the distal tip 414d of the catheter lumen 414. The body 410 may also increase resistance. As pressure in the elongate lumen 404 builds, the cryogens are forced out of the elongate lumen 404, through the first end 406c, and into the extension lumens 408. The cryogens then exit the second end 406r in a cryospray that is in closer proximity to the target tissue 432 than the exits of the radial apertures 416 without the extension members 406. In some cases, the extension members may increase the effective profile of a catheter by up to at least 50%, or from about 5% to 100%, or more.

In various embodiments, described here or otherwise, within the scope of the present disclosure, the proximal portion of the body may be shaped to help distribute the spray evenly all around the elongate lumen, e.g., a convex or concave shape. The distal portion of the body may take on several shapes. An atraumatic shape such as a dome may reduce the risk of trauma to the patient, reducing the risk of abrasions, perforations, etc., and/or reduce the risk of damaging the catheter within the working channel or the endoscope or vice versa. Various overall diameters of the body may be adjusted to cover the distal end of a catheter tip in order to protect the patient, device or endoscope.

In various embodiments, described here or otherwise, within the scope of the present disclosure, there may be any number of extension members. The number of extension members could match up with the number of radial apertures in the catheter, but there could be less than the number of apertures in the catheter. With fewer extension members than radial apertures, some of the catheter apertures may be blocked, increasing the flow rate through the extension members. Merely one extension member may be used for targeted treatment of a target tissue. The extension members may take on various shapes and angles. The extension members may be angled non-radially to adjust the cryospray pattern, e.g., proximally or distally. The second ends of the extension members may include nozzles of various shapes to further restrict and direct cryospray flow. The extension members may vary in thickness to adjust overall strength. The extension members may have various outer diameters that may be significantly smaller than the radial apertures in order to further restrict flow while the outer surface of elongate member blocks the unfilled portion of the radial aperture. The extension members may have a relaxed state, where they lay substantially parallel to the catheter lumen in a relaxed state along the elongate member or catheter, and an activated or extended state when fluid is forcibly supplied through the elongate lumen where they are partially or substantially straightened in an upright position and extend radially outward in an activated state. The extension members may extend radially with respect to a central axis of the elongate lumen. The extension members may be integral with the elongate member.

In various embodiments, the extension device may be held within a catheter via frictional forces between the outer surface of the elongate member and the inner surface of the catheter lumen. The extension members may also fix the extension device in place via resistance from the radial apertures on the extension members in the proximal direction. An adhesive applied to the elongate member, the body, or at least one of the extension members may fix the extension device in position within the catheter. The elongate member may be configured for insertion into the distal end of a catheter, e.g., curved edges at a proximal end of the elongate member may ease insertion. The extension members may be overmolded to a device and/or a catheter.

In various embodiments, described here or otherwise, within the scope of the present disclosure, a catheter may have a first open end, a second end, a catheter lumen therebetween, and at least one radial aperture at the second end. The catheter may include at least one extension member extending from the at least one radial aperture with a first open end in fluid communication with the catheter lumen and a second end open end with an extension lumen therebetween. The extension member(s) may extend from a body that is integral with the catheter. Alternatively, the extension member(s) may extend from a body that is inserted into the second end of the catheter in accordance with an embodiment of the disclosure.

Figure 5A:
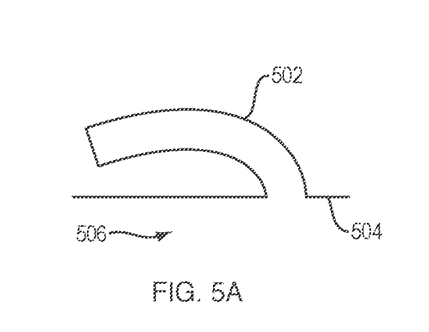
FIGS. 5A and 5B illustrate an embodiment of an extension member for extension devices in accordance with the present disclosure.
Figure 5B:
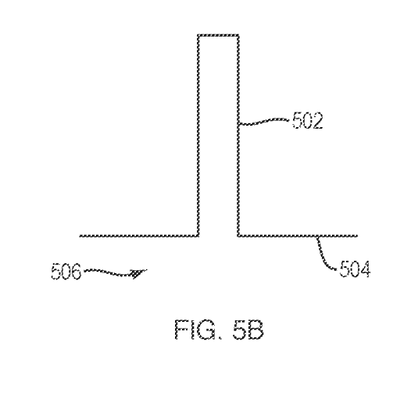

Referring to FIGS. 5A and 5B, an embodiment of an extension member for an extension device according to the present disclosure includes an extension member 502 attached to an elongate member 504. The extension member 502 may lay substantially parallel to the catheter lumen along the elongate member 504 or catheter in a relaxed state as illustrated in FIG. 5A. The extension member 502 is in the relaxed state when there is no fluid flow through the extension member 502. The extension member 502 may be thin-walled so as to lay limp under its own weight. The extension member 502 may be biased to face a proximal direction when in the relaxed state to case distal insertion of the catheter into an endoscope and/or patient. The elongate member 504 may be more rigid so as to maintain the shape of the elongate lumen 506. The extension member 502 may be in the activated, or extended state, when a fluid is flowed through the extension member 502, as illustrated in FIG. 5B. The extension member 502 is substantially straight in this state.

Figure 6A:
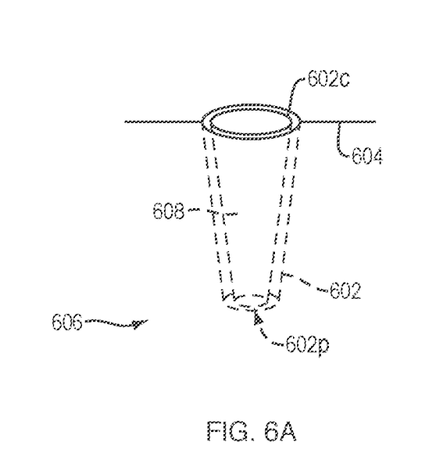
FIGS. 6A-6C illustrate embodiments of an extension member for extension devices in accordance with the present disclosure.
Figure 6B:
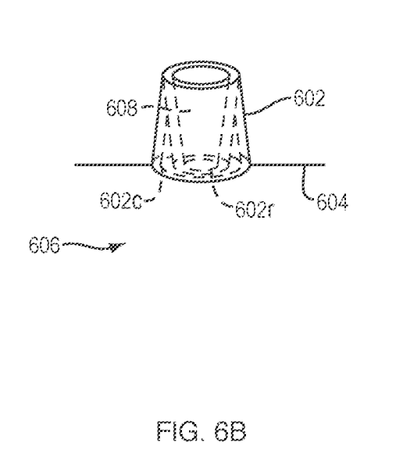
Figure 6C:
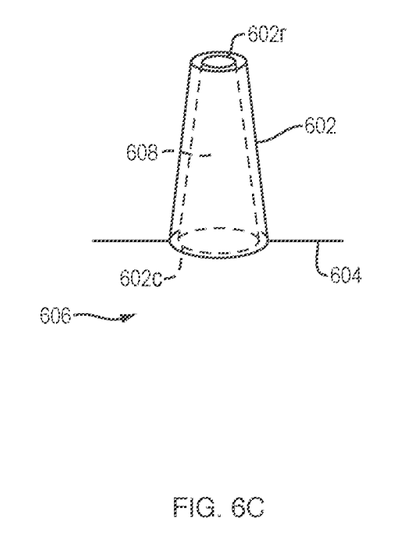

Referring to FIGS. 6A through 6C, embodiments of extension members for extension devices according to the present disclosure include an extension member 602 with an extension lumen 608 having a diminishing diameter that diminishes from the first end 602c toward the second end 602r. The extension member 602 may invert into the elongate lumen 606 of the elongate member 604 in the relaxed/inverted state, as illustrated in FIG. 6A. The extension member 602 may extend out of the elongate lumen 606 and away from the elongate member 604 in the extended/excited state as illustrated in FIG. 6C. The extension member 602 may extend out of the elongate lumen 606 and partially away from the elongate member 604, while still being partially inverted within the extension lumen 608, in the extended or partially extended state as illustrated in 6B. The configuration illustrated in FIG. 6B may be achieved by a low flow of fluid through the extension lumen 608 or it may be achieved by the extension member 602 colliding with an object or tissue before fully extending.

The embodiments described herein may be made of silicone, nitinol, spring steel wire, and the like, or a combination thereof. Various thicknesses may be used to achieve a desired rigidity of some parts over others. For example, the walls of the elongate member may be thicker than the walls of the extension member such that the elongate member substantially maintains its shape while the extension member is limp and pliable. The extension member may be made of any pliable and polymeric material (e.g., silicone), which is biocompatible and compatible with a fluid (e.g., cryogen) traveling from the elongate member and/or catheter through the extension member. The extension member may be a metallic tube, for example, superelastic nitinol, or the like. The extension member may be welded, bonded, and/or friction fit to the radial apertures. For some systems, such as with low pressure flows, the extension member may spring out to a desired orientation. This may be accomplished by delivering a device in a sheath and retracting the sheath to allow the spring structure of the extension member to actuate.

An embodiment of a method of enhancing spray from a catheter may include inserting a device with at least one extension member into a distal end of the catheter. The device may be rotated such that at least one extension member substantially lines up with at least one radial aperture of the catheter. Alternatively, the catheter may be manufactured with the extension device body in place or the extension member(s) may be integral with the catheter lumen. The device may be held in place while a medical professional introduces a fluid into a proximal end of the catheter. The fluid may have enough pressure to extend the at least one extension member through the at least one radial aperture. The device and/or catheter may be inserted into the body lumen of a patient. A treatment fluid, e.g., cryogen, may be introduced into a proximal end of the catheter. The treatment fluid may be at a pressure high enough to extend the at least one extension member into a substantially straight configuration.

Figure 7A:
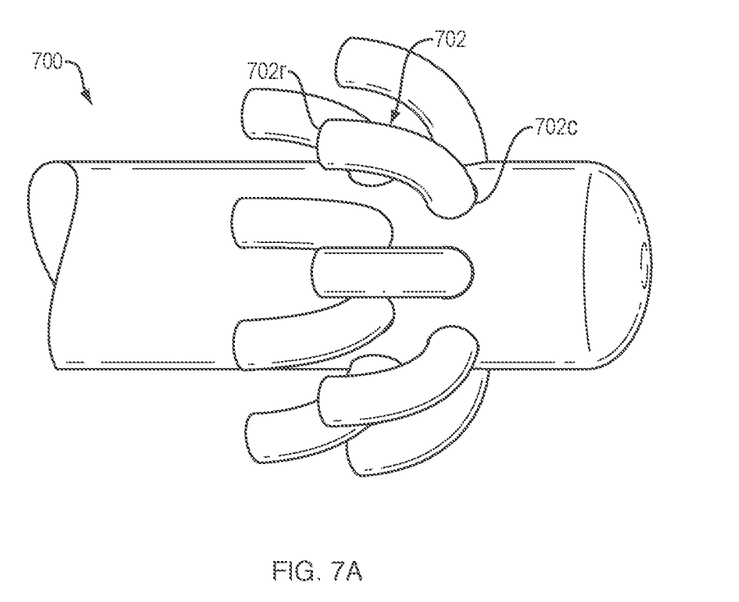
FIGS. 7A-7B illustrate embodiments of an extension catheter in accordance with the present disclosure.

Referring to FIG. 7A, an embodiment of an extension catheter according to the present disclosure includes extension members 702 that may be configured to lay substantially parallel to a lumen of a catheter 700 in a relaxed state and extend radially outward in an activated state. The extension members 702 may be integral with the catheter or an extension device may be an accessory or part of a kit with the catheter 700. The first end 702c of the extension members is in fluid communication with the lumen of the catheter 700. The second end 702r is biased proximally when the extension members are in a relaxed state. FIG. 7A illustrates the extension members 702 in a relaxed state.

Figure 7B:
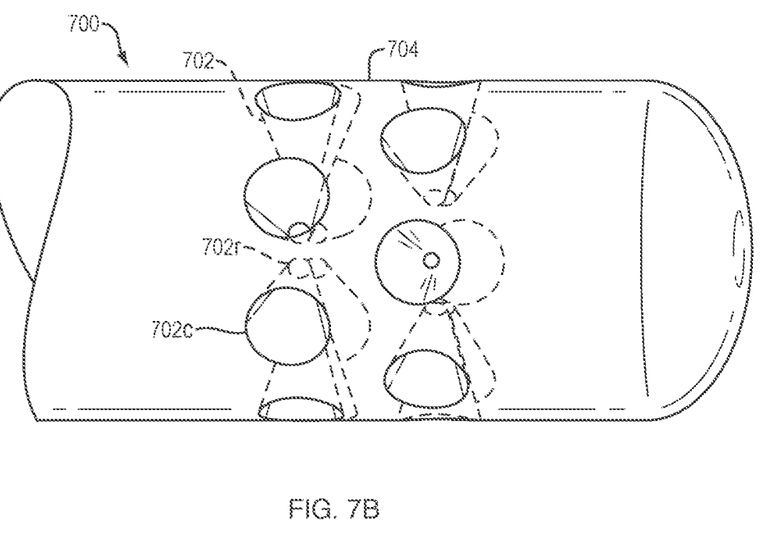

Referring to FIG. 7B, an embodiment of an extension catheter according to the present disclosure includes extension members 702 with a second open end 702r of the extension members 702 that is inverted within the lumen of the catheter 700 in an inverted state. The extension members 702 may be integral with the catheter or an extension device may be an accessory or part of a kit with the catheter 700. The extension members 702 may extend outward from the catheter 700 in an extended state. The extension lumen 704 of the extension members 704 have a diminishing diameter that diminishes from the first end 702c to the second end 702r. FIG. 7B illustrates the extension members 702 in an inverted state. The extension members 702 may have a length that is configured to extend an effective diameter of the catheter 700 by at least 50%

All of the devices and/or methods disclosed and claimed herein can be made and executed without undue experimentation in light of the present disclosure. While the devices and methods of this disclosure have been described in terms of preferred embodiments, it will be apparent to those of skill in the art that variations can be applied to the devices and/or methods and in the steps or in the sequence of steps of the method described herein without departing from the spirit and scope of the disclosure. All such similar substitutes and modifications apparent to those skilled in the art are deemed to be within the spirit and scope of the disclosure as defined by the appended claims.

What is claimed is:

1. An extension device for a radial spray catheter comprising:
    an elongate member with a first open end, a second end, and an elongate lumen therebetween; and
    at least one extension member extending from the elongate member with a first open end in fluid communication with the elongate lumen at one end, a second open end, and an extension lumen therebetween,
    wherein the at least one extension member is configured to lay substantially parallel to the elongate lumen in a relaxed state and extend radially outward in an activated state, and wherein the at least one extension member is configured to substantially align with at least one radial aperture in a distal end of the radial spray catheter.

2. The device of claim 1, wherein the second end of the elongate member is closed.

3. The device of claim 2, further comprising a body at the second end of the elongate member with a diameter larger than a diameter of an outer surface of the elongate member.

4. The device of claim 3, wherein the body has an outer diameter that is dimensioned to be larger than a spray lumen of the radial spray catheter.

5. The device of claim 1, wherein the at least one extension member extends radially with respect to a central axis of the elongate lumen.

6. The device of claim 1, wherein the at least one extension member is integral with the elongate member.

7. The device of claim 1, wherein the at least one extension member has a length that is configured to extend an effective diameter of a catheter by at least 50%.

8. The device of claim 1, wherein the radial spray catheter is a cryospray catheter that delivers cryospray through the at least one radial aperture.

9. The device of claim 1, wherein the activated state comprises a cryospray being delivered under pressure through the extension lumen, and the second end of the at least one extension member is configured to be spaced contactless with tissue in the activated state.

10. An extension device for a radial spray catheter comprising:
- an elongate member with a proximal open end, a closed distal end, and an elongate lumen therebetween; and
- at least one extension member extending from the elongate member with a first open end in fluid communication with the elongate lumen, a second open end, and an extension lumen therebetween, wherein the second open end of the at least one extension member is inverted within the extension lumen in the inverted state and extended outward from the extension lumen in the extended state, and wherein the at least one extension member has an inverted state and an extended state.

11. The device of claim 10, wherein the at least one extension member is configured to substantially align with at least one radial aperture in a distal end of the catheter.

12. The device of claim 10, wherein the extension lumen has a diminishing diameter that diminishes from the first end to the second end.

13. The device of claim 10, wherein the at least one extension member is inverted within the elongate member in the inverted state and extends radially outward from the elongate member in the extended state.

14. A radial extension catheter for radial spray comprising:
- a catheter with a first open end, a second end, and a catheter lumen therebetween;
- at least one radial aperture at the second end; and
- at least one extension member extending from the at least one radial aperture with a first open end in fluid communication with the catheter lumen, a second open end, and an extension lumen therebetween, wherein the at least one extension member has a length that is configured to extend an effective diameter of the catheter by at least 50%.

15. The catheter of claim 14, wherein the at least one extension member is integral with the catheter lumen.

16. The catheter of claim 14, wherein the second open end of the at least one extension member is inverted within the catheter lumen in an inverted state and is extended outward from the catheter lumen in an extended state.

17. The catheter of claim 14, wherein the extension lumen has a diminishing diameter that diminishes from the first end to the second end.

* * * * *